United States Patent [19]

Näsman et al.

[11] Patent Number: 5,300,604

[45] Date of Patent: Apr. 5, 1994

[54] PROCESS FOR MAKING A MACROPOROUS STYRENE POLYMER

[76] Inventors: Jan-Anders H. Näsman, Rakuunatie 58 a C 48, SF-20720 Turku; Osmo Hormi, Kaitoväylä 32 A 14, SF-90570 Oulu; Esko Pajunen, YO-kylä 18 A 4, SF-20540 Turku; Mats J. Sundell, Kuppisgatan 89 b 8, SF-20510 Turku, all of Finland

[21] Appl. No.: 989,155

[22] Filed: Dec. 11, 1992

Related U.S. Application Data

[63] Continuation-in-part of Ser. No. 823,326, Jan. 21, 1992, Pat. No. 5,200,554.

[51] Int. Cl.$^5$ ............................................. C08F 30/02
[52] U.S. Cl. ................................................... 526/278
[58] Field of Search ...................... 562/21, 22; 526/278

[56] References Cited

U.S. PATENT DOCUMENTS

| | | | |
|---|---|---|---|
| 3,993,635 | 11/1976 | Mango, III | 526/278 |
| 4,444,969 | 4/1984 | Younes | 526/278 |
| 4,732,998 | 3/1988 | Binderup . | |
| 5,116,882 | 5/1992 | Grey et al. | 526/278 |

FOREIGN PATENT DOCUMENTS

| | | | |
|---|---|---|---|
| 739996 | 8/1966 | Canada | 526/278 |
| 216681 | 4/1987 | European Pat. Off. . | |
| 324421 | 7/1987 | European Pat. Off. | 562/21 |
| 3942641 | 2/1991 | Fed. Rep. of Germany | 526/278 |
| 62-263210 | 11/1987 | Japan | 526/278 |
| 252335 | 3/1970 | U.S.S.R. | 526/278 |
| 328104 | 11/1972 | U.S.S.R. . | |
| 0621679 | 8/1978 | U.S.S.R. | 526/278 |
| 877905 | 9/1961 | United Kingdom | 526/277 |
| 2-089807 | 6/1982 | United Kingdom | 562/21 |

OTHER PUBLICATIONS

Menger et al., J. Am. Chem. Soc. 1990, 112, 6723–6724.

*Primary Examiner*—Joseph L. Schofer
*Assistant Examiner*—N. Sarofin
*Attorney, Agent, or Firm*—Wolf, Greenfield & Sacks

[57] ABSTRACT

The invention relates to novel methylene bisphosphonic acid derivatives carrying a styrene group attached to the methylene carbon. The novel compounds are useful e.g. for functionalizing polymers of styrene type, especially macroporous styrene polymers, by copolymerizing the novel derivative with styrene and optional crosslinking agents. The invention also provides for new crosslinking agents especially suitable for the said purpose.

16 Claims, No Drawings

PROCESS FOR MAKING A MACROPOROUS STYRENE POLYMER

This is a continuation-in-part of U.S. Patent application Ser. No. 07/823,326 filed Jan. 21, 1992 for Novel Bisphosphonic Acid Derivatives And Their Use by the same applicants now U.S. Pat. No, 5,200,554, the disclosure of which is expressly incorporated herein by reference, and this is a continuation-in part of Applicants' U.S. patent application for Novel Cross-Linking Agents And Their Use which is being filed concurrently on the same date, the disclosure of which is incorporated herein by reference.

FIELD OF INVENTION

This invention relates to a novel type of bisphosphonic acid derivatives, more specifically to methylene bisphosphonic acid derivatives substituted at the methylene carbon with an optionally bridged vinylbenzyl group. The invention also relates to the use of the novel compounds for making functionally modified, preferably macroporous styrene polymers. The invention further relates to making functionally modified, mechanically durable styrene polymers crosslinked with a bis(-vinylphenyl)-type compound, as well as a group of novel crosslinking agents. The said reactive polymers find a variety of use, e.g. as a support for catalysts in chemical reactions and in separation technology.

BACKGROUND OF THE INVENTION

Functional groups may be attached to a polymer chain according to two methods: by functionalizing during manufacture of the polymer, i.e. by copolymerizing with a monomer carrying the functional group, or by modifying the chain chemically. The latter method is the one most in use today, but the former has a number of advantages, one being that the number of manufacturing steps and thus side product formation can be reduced.

Porous or macroporous styrene materials are structures formed by agglomerated microspheres (100–200 nm) consisting in turn of cores (10–30 nm) (Jacobelli H., Guyot A., Angew. Makrom. Chem., 80, (1979), 31). Both between the cores and the agglomerates there are interconnected pores which provide for the large surface area of the polymer. These polymers have found a number of applications, especially within organic chemistry in the form of polymer bound catalysts, reagents and in chromatographic separation processes. Polymer bound enzymes, controlled dosage of medicines, pesticides and cosmetics are also used. The materials also find use for the purification of water, other liquids and gases.

Although the research regarding polymer bound reagents is very intensive, there are today only a few industrial applications in use. The reason for this is, from a polymer chemical point of view, three, namely diffusion restrictions within the polymer, insufficient mechanical characteristics and insufficient chemical inertness of the material. Diffusion restriction within the polymer makes the activity of the reagent low, if the diffusion rate into and out from the polymer becomes the rate controlling step. Insufficient mechanical strength makes the polymer break down, difficult to separate and re-use. Functional residues, side products and remaining double bonds can poison the polymer or break it down so that the functional groups and the activity are lost.

In order to obtain a pure product and good process economy it is important to keep the manufacturing steps as few as possible. Consequently, copolymerization of a monomer carrying the functional groups would be a feasible alternative for the synthesis of polymer, especially macroporous polymer supported species. However, until now it has not been possible to manufacture satisfactory products by copolymerization as the functional groups have, to a major degree, been locked within the polymer structure and are thus not available for reaction.

Macroporous polymers are mostly made by polymerizing a monomer and a crosslinking agent in the presence of a solvent which dissolves the monomers but not the polymer formed. Porous structures with interconnected pores can also be synthesized from water-in-monomer-emulsions in the presence of a surfactant. The latter method provides for very porous materials with larger pores and a more even, homogeneous pore structure than the former method.

An applicable method for the preparation of polymers with a high degree of porosity is described in J. Chem. Soc. Chem. Comm., 7, (1990), 1589, and in the EP-patent 0060138. Materials of this type are very attractive for the preparation of polymers with a grafted polymer layer within the pores.

In the publication J. Am. Chem. Soc., 112, (1990), 1263, Menger et al., there is disclosed a method for polymerizing styrene and divinyl benzene in a system were the water in monomer emulsion is a microemulsion. — The term "microemulsion" has been defined (Danielsson et al., Colloids Surfaces, 3, (1981), 391) as a system consisting of water, oil and an amphiphilic compound, which forms a single optical isotrope and a thermodynamically stable solution. The microemulsion is made using as the surfactant i.a. sodium bis(2-ethylhexyl)sulfosuccinate (AOT).

In a later article, J. Am. Chem. Soc., 112, (1990), 6723, Menger et al. also described a method for controlling the location of the functional groups to the pore surfaces of the polymer. As the monomer carrying the functional group, a styrene derivative was used, having a, dimethyl amine group at the end of a chain attached to the phenyl group. Although the process described can be considered to give satisfactory products for some purposes, it has the drawback that the functional monomer used is excessively soluble in the styrene phase, wherefore its concentration in the pore forming water pools is reduced. Consequently the number of available functional groups in the final polymer is also reduced.

The aim of the present invention is i.a. to provide a new type of functionalizing monomers having superior and interesting complexing properties, and by means of which it is possible to achieve an increased degree of surface functionalization, and especially when used in the manufacture of macroporous styrene polymers, e.g. using the microemulsion polymerization technique.

SUMMARY OF THE INVENTION

The object of the present invention is a new group of methylenebisphosphonic acid derivatives of the general formula

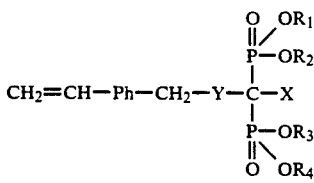

(I)

wherein each one of the groups $R_1$, $R_2$, $R_3$ and $R_4$ has the meaning of hydrogen or lower alkyl or has the meaning of $-CH_2CH_2OH$, or wherein each one of the pair of groups $R_1-R_2$ and/or $R_3-R_4$ has the meaning of $-CH_2CH_2-$, X has the meaning of hydrogen, methyl, ethyl or COOH, Y has the meaning of an optionally unsaturated alkylene group $-(CH_2)_n-$ where n has the value 0 to 12, or has the meaning of $-OCH_2CH_2O-$, or has the meaning of $-OCH_2C^*H(OH)CH_2-$ where the marked carbon atom is chiral and can exist in R- or S-form or as a racemate, Ph means a phenyl group which carries the vinyl group in meta- or para position to the methylene group, as well as their salts and complexes with metals.

The compounds (I) can thus be in free acid form, in ester form (one or more of the groups $R_1$, $R_2$, $R_3$ and $R_4$ is different from hydrogen), and/or in salt form as well as complexed to metals, especially to transition metals, such as to palladium, rhutenium, and platinum, but also to radioisotopes, for example.

Lower alkyl contains generally 1 to 4C-atoms.

X is advantageously hydrogen or methyl. Y is in its simplest form a direct bond (n=0) but may also be an optionally unsaturated alkylene group of 1 to 12 C-atoms, such as methylene. By varying the length of the group Y it is possible to regulate the the hydrophil/lipophil balance (HLB) and with certain solvents or surfactants, a longer chain e.g. with 6 to 12 C-atoms can be favourable.

An advantageous compound of the formula I is 1-(3-vinylphenyl)propane-2,2-bis(phosphonic acid) or its isomer 1-(4-vinylphenyl)propane-2,2-bis(phosphonic acid).

The favourable properties of the compound I which makes them function well as a functionalizing compound are that they contain the double bond (vinyl) necessary for functionalization by polymerization. Another favourable property is that the double bond is separated from the bis(phosphonic acid/ester) moiety by the spacer group $PhCH_2$, which makes the compound I a good monomer for copolymerization with styrene. A third favourable property is the bis(phosphonic acid/ester) moiety that is necessary for complexation to metals, the complexation process showing selectivity between different metals, which is of importance, for example, in the extraction of metals.

The new compounds I may be prepared in a manner known as such, for example by nucleophilic substitution of the chlorine in chloromethyl styrene by addition of the sodium salt of a corresponding bis(phosphonic ester). Another example is addition of the said salt to an appropriate acceptor such as an epoxide, the so formed product reacting with chloromethyl styrene to give compounds I.

The procedure can start from an appropriate dialkyl phosphite, which can be a commercial product or is in turn prepared from phosphorus trichloride or amide and an alcohol, The dialkylphosphite or 2-oxo-1,3,2-dioxaphospholane is reacted under basic conditions with methylene chloride to give tetra-alkylbis(phosphonate) (Hormi et al., Synth. Comm. 1990, (1865-1867), which, if desired, can be condensed with an aldehyde using a catalyst to form a tetraalkyl alkenylidene bisphosphonate (Degenhardt et al., J. Org. Chem. 1986, 51, 3488).

The acidic hydrogen on the carbon atom between the two phosphorus atoms is removed with a strong base, e.g. sodium hydride, to form an anion, which is reacted with the appropriate electrophilic moiety, e.g. the $CH_2Cl-$group of chloromethyl styrene or the epoxide group of 2,3-epoxypropyl vinylbenzyl ether (Tomoi et al., Macromol. Chem. Rapid Comm., 1986, 7, 143). The tetraalkyl esters obtained may be hydrolyzed directly with water or in slightly acidic or basic conditions if in the form of a five-ring (J. Am. Chem. Soc. 1991, 113, 5713 and references therein) to give the half-esters, or the tetraalkyl esters are converted to trimethylsilyl (TMS) esters by reacting with trimethylsilyl chloride under phase transfer conditions. The TMS-esters are proned to hydrolysis under slightly acidic conditions.

When X is COOH, the anion of tetraalkyl bis(phosphonate) is allowed to react with a chloroformate to give a compound substituted at the former methylene carbon with a ROOC-group, the acidic methine carbon of the compound is removed and the so formed anion is allowed to react with an electrophilic moiety as above and the carboxylic ester group is hydrolyzed carefully.

The anion of a tetraalkyl bisphosphonate can also be reacted with an epoxide to introduce e.g. a 1-hydroxy ethyl group at the methylene carbon, which can be allowed to react with an appropriate electrophilic moiety as described above.

Terpolymerisation of e.g. 1-vinylphenylpropane-2,2-bisphosphonic acid, styrene and divinylbenzene (DVB) is complicated by the fact that the bis(phosphonic acid) monomer is completely insoluble in the styrene monomers. However, the monomer is quite soluble in a water/AOT/styrene $-$DVB microemulsion. For example it is possible to solubilize up to 15 wt-% of 1-vinylphenylpropane-2,2-bisphosphonic acid of the total monomer content, in a 5 wt-% water, 15 wt-% AOT microemulsion. These values are remarkably high compared to the fact that pure water can solubilize only up to approx. 10 wt-% of functional monomer, and a solution of 15 wt-% AOT in styrene none at all.

The compounds of the formula I are insoluble in styrene, wherefore they are especially suitable for use in polymerizing styrene in microemulsion, as described earlier. According to this method, styrene and the crosslinking monomer are mixed, the crosslinking agent being used in an amount of at least 10 mole-% calculated on all monomers, generally at an amount of 20 to 40 mole-%. Thereafter a surfactant is added, whereby any surfactant suitable for use in a microemulsion system can be used, such as for example bis(2-ethylhexyl)-sulfosuccinate, or dimethyldioctadecylammonium bromide. The amount of surfactant can vary between 1 and 50 wt-% of the monomer phase, generally 5 to 20 wt-%. Thereafter water is added. The amount of water, when using AOT, is $[H_2O]/[AOT]<30$. In case higher amounts are used, a two-phase system will form. To the formed emulsion the functional monomer is added. The amount of functional monomer naturally depends on the degree of functionalization desired, but generally up to 20 wt-% of the total monomer phase can be used.

The mixture is slightly shaken and warmed (40° C.) and allowed to polymerize with AIBN (azoisobutyronitrile) as initiator in 60° C. for 10 hours. The formed polymer is ground into a powder in a laboratory mill fitted with a filter, extracted in methanol and toluene and dried thoroughly in vacuum.

Due to the insolubility of the functional monomer in the styrene phase, it will be enriched to the surfactant layer in the water filled pores. Using the novel functionalizing monomers of the invention, it has been possible to direct 75 to 100% of the bis(phosphonic acid) groups to the pore surfaces as compared to 51% obtained by Menger et al. using the same surfactant and a styrene-soluble functional monomer.

Using the novel functionalizing monomers of the invention it is also possible to synthesize porous surface functionalized styrene polymers using conventional per se known solvent polymerization techniques. The ratio of monomer to crosslinking agent, as well as the amount of functionalizing monomer, are the same as those mentioned in connection with the microemulsion technique. As a solvent, in which the monomers are soluble, but the formed polymer is insoluble and thus precipitates after formation, alcohols such as butanol, heptanol, hexanol, or organic acids, such as ethyl caproic acid, may be mentioned. The amount of solvent used may vary but is generally from 20 to 60 wt-% of the total monomer phase. Due to the insolubility of the bis(phosphonic acid) monomer in the styrene phase, it will be enriched in the solvent filled pores which are formed in the material during polymerization. The lipophilic part of the molecule will be attracted to the non-polar styrene phase and the functional monomer will thus attach by polymerization to the pore surfaces. The functionalizing monomer is in this case advantageously added to the monomer mixture dissolved in the solvent used.

According to a preferred embodiment, a compound of the formula I, wherein $R_1$-$R_4$ as defined, is used for the preparation of the functionalized polymer, of which, in a subsequent step, a salt or a complex with a suitable metal, such as a transition metal, is formed, optionally including an ion-exchange reaction, or, when necessary ($R_1$-$R_4$ not H), a preceeding hydrolysis to convert at least one of said R-groups to H.

The crosslinking agent used for polymerization is generally described as being of divinyl-type, such as a compound of divinylbenzene type, such as DVB, or e.g. of distyryl type.

Divinylbenzene is the most common crosslinking agent used with styrene and it is a commercially available compound. However, due to the high difference in reactivity between divinyl benzene and styrene, the distribution of crosslinks in the macroporous polystyrene is heterogeneous. That is, in the polymer there are formed strongly crosslinked cores bound to only weakly crosslinked or noncrosslinked polymer. The cores contain a number of unreacted double bonds which for sterical reasons have not been able to polymerize. The heterogenous structure affects adversely the mechanical characteristics of the polymer.

Styrene, especially macroporous styrene polymers of improved mechanical strength may, however, be obtained when using as a crosslinking agent a compound containing two vinylbenzyl groups at each end of a chain, which may be an alkylene chain optionally broken by a heteroatom, such as oxygen, or it may be a polymer. Such a crosslinking agent may e.g. have the formula $$CH_2=CH-Ph-(CH_2-O)_{m'}-(CH_2)_m- -(O-CH_2)_{m'}-Ph-CH=CH_2 \quad (II)$$

wherein, when m=0, m' is an integer 1 to 12, and when m=1, m is an integer 2 to 12. The vinyl group is in the meta or para-position of the phenyl group Ph with respect to the methylene group.

Especially good results have been obtained with the following compounds:

1,2-bis(vinylphenyl)ethane
1,6-di(vinylbenzyloxy)hexane
1,12-di(vinylbenzyloxy)dodecane When m=0, the compounds are bis(vinylphenyl)alkanes. Of these, compounds wherein m, is 6 and 10 are known from the SU-patent 328 104 for copolymerization with styrene in suspension.

When in the formula (II) m=1, the compounds are bis(vinylbenzyloxy)alkanes. These compounds are new, and as such form part of the invention. These compounds have the advantage over the bis(vinylphenyl)alkanes that they are easily manufactured from commercially available vinylbenzyl chloride and diols.

The bis(vinylphenyl) crosslinking agents, wherein m=0, may be prepared by coupling of the corresponding vinylphenylalkyl chloride according to Wurtz in the presence of magnesium turnings and iodine. The compounds wherein m=1 on the other hand may be prepared from vinylbenzyl chloride and the corresponding 1,m'-diols, in a manner known per se.

Using the crosslinking monomers of the invention, it is possible to obtain a styrene polymer crosslinked to any desired degree. The polymeric network can be synthesized using the same, well known, methods of styrene divinylbenzene copolymerization. Compared to the latter the new crosslinked polymers have good mechanical strength and a homogeneous distribution of crosslinks. The ratio of crosslinking agent to other monomers should, as stated above, be at least 10% on a molar basis to obtain macroporous polymers, preferably 20-40 %.

DETAILED DESCRIPTION OF THE INVENTION

In the following Examples, which are not intended to be limiting in any way, the invention will be described in more detail.

EXAMPLE 1

Preparation of 1-(3-vinylphenyl)propane-2,2-bisphosphonic acid 1-(3-vinylphenyl)propane-2,2-bisphosphonic acid (6), i.e. a mixture of the 3- and 4-vinylphenyl compounds, was prepared according to the following Scheme 1:

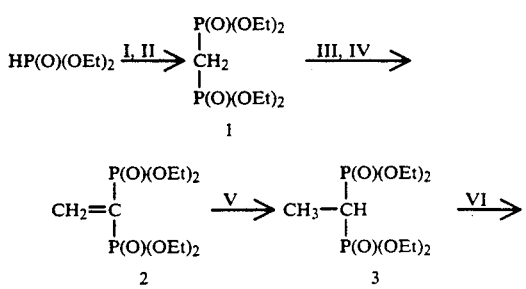

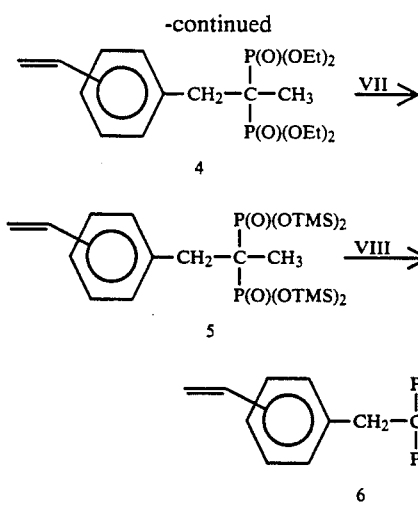

```
I    EtONa, EtOH              V    H₂, Pd, EtOH
II   CH₂Cl₂                   VI   NaH, toluene,
                                   CH₂=CH—C₆H₄—CH₂Cl
III  (CH₂O)ₓ, MeOH, HNEt₂    VII  ClSiMe₃, KBr, Bu₄NBr
IV   p-Me—C₆H₄SO₃H, toluene  VIII HOAc:THF:H₂O (3:1:1)
```

Tetraethyl methylenebisphosphonate (1) was prepared from sodium diethylphosphite and dichloromethane (Synthetic Communications, 20(12), (1990), 1865-7) at a yield of about 50%. From the compound (1) tetraethyl ethenylidenebisphosphonate (2) was synthesized using the two-step procedure of Degenhardt and Burdsall (J. Org. Chem. 51, (1986), 3488-90). First one prepares from the compound (1), paraformaldehyde and methanol, using diethylamine as a catalyst, tetraethyl 2-methoxy-ethane-1,1-bisphosphonate. Then methanol is eliminated with paratoluene sulphonic acid in toluene, and the compound (2) is obtained in 79% yield.

The compound (2) was hydrogenated in aliquots of 20 g to tetraethyl ethane-1,1-bisphosphonate (3) as follows: 19.8 g of the compound- (2), 200 ml of abs. ethanol and 1.9 to 2.0 g of 10% palladium on activated charcoal (Fluka 75990) was placed in the hydrogenation vessel, provided with a magnetic stirrer, and connected to a gas burette that maintained the reaction at 1 atmospheric hydrogen pressure. Stirring was started and the air in the system was displaced by repeating the process of evacuating and flushing with hydrogen several times. Then an adequate amount of hydrogen was stored in the gas burette and the stirring was continued at room temperature until the consumption of hydrogen ceased. After 2 hours the mixture was filtrated through silica gel, and the gel was washed with ethanol, and the filtrate was concentrated on a rotary vacuum evaporator. Although the raw product was fairly pure, it was distilled at reduced pressure. The distillation was carried out only after collecting the evaporation residues from several hydrogenation fractions. For example, from 67.5 g (0.225 moles) of compound (2), 64.6 g (95 %) raw product (3) was obtained after evaporation, and 62.2 g (92 %) after distillation; b.p. 95-97 ° C./0.05 mmHg; ¹H NMR (CDCl₃, 400 MHz) 4.19 (two overlapping q, 8H, OCH₂, $J_{HH}$=7.3, $J_{HP}$=7.3), 2.40 (tq, 1H, CH, $J_{HH}$=7.7, $J_{HP}$=23.2), 1.47 (td, 3H, CH₃CH, $J_{HH}$=7.4, $J_{HP}$=17.1), and 1.35 (t, 12H, CH₂CH₃, $J_{HH}$=7.1); m/e$_{theor.}$ 302.1048 and m/e$_{exp.}$ 302.1062.

Tetraethyl 1-(vinylphenyl)propane-2,2-bisphosphonate (4) was prepared from compound (3) and vinylbenzyl chloride, of which 70% was in meta- and 30% in para-form, in the following manner. In a flame dried two-necked flask equipped with a dropping funnel and protected with nitrogen gas 100 ml of dry toluene and 2.69 g (0.112 moles) of dry sodium hydride were introduced. Mixing was started and 30.0 g (0.099 moles) of compound (3) was dropped to the mixture. When the addition was complete and the release of hydrogen had ceased, stirring was continued for an additional hour at room temperature. Thereafter 18.3 g (0.12 moles) of vinylbenzyl chloride was dropped to the mixture, and stirring was continued under the protective gas at room temperature until the reaction was complete. This lasted from one to two weeks. The reaction mixture was concentrated on a rotary vacuum evaporator. The residue was dissolved in diethyl ether, washed three times with water, dried over sodium sulphate and the solvent evaporated in vacuum. 33.5 g (81%) of the raw product (4) was obtained, of which about 80 % was compound (4) and 20% vinylbenzyl chloride. The raw product was used unpurified in the subsequent reaction.

The compound (4) was silylated in the following manner: 33.5 g (0.0800 moles) of the raw product (4), 55 g (0.46 moles) of potassium bromide dried at 110° C. in an oven, about 150 ml of trimethylchlorosilane and an amount of tetrabutylammonium bromide corresponding to the tip of a spatula were weighed into a flame dried round flask.

Nitrogen was used as a protective gas. The mixture was refluxed while continuously stirring vigorously. In order to accelerate the reaction, dry potassium bromide and tetrabutylammonium bromide were added at intervals. The reaction lasted 1 to 2 weeks. When the reaction was complete, the solution was decanted, and to the solid residue petrol ether (b.p. 40° to 60° C.) was added, the resulting mixture stirred and redecanted. The same procedure was repeated several times. The solutions were combined and excess trimethylchlorosilane and solvents were removed by distillation at reduced pressure. 43.3 g (91%) of a distillation residue, i.e. raw compound (5) was obtained. It was used as such in the subsequent reaction.

The raw compound (5) (43.3 g, 0.073 moles) was hydrolyzed in 100 ml of an acetic acid-tetrahydrofurane-water (3:1:1) -mixture. The mixture was vigorously stirred at room temperature for a few hours (such as over night). Then the solvents were evaporated in vacuum, and the solid residue was suspended in ethyl acetate in which compound (6) is poorly soluble. The mixture was centrifuged for 10 min at 2500-3000 rpm and decanted. The same treatment was repeated altogether five times. The ethyl acetate residues were evaporated from the solid white residue. Thereby 12.0 g (54 %) of pure compound (6) was obtained, of which about 70 % was meta-substituted compound (6); ¹H NMR (DMSO, 400 MHz) 8.6-8.1 (m. 4H, OH), 7.38-7.16 (m, 4H, Ar), 6.71 (dd, 1H, =CH—Ar, $J_{HHcis}$=10.9, $J_{HHtrans}$=17.6), 5.78 (dd, 1H, H$_{cis}$C=C—Ar, $J_{HHtrans}$=17.6, $J_{HHgem}$=0.8), 5.24 (dd, 1H, H$_{trans}$C=C-Ar, $J_{HHcis}$=10.9, $J_{HHgem}$=0.8), 3.14 (t, 2H, CH₂—Ar, $J_{HP}$=14.8), 1.22 (t, 3H, CH₃, $J_{HP}$=16.4), and 30% para-substituted one, which ¹H NMR (DMSO, 400 MHz)-spectrum differs from that of meta-compound in the following chemical shifts (when the shifts of aromatic hydrogens have not been analyzed); 5.79 (dd, H$_{cis}$C=C-Ar), 5.22 (dd, H$_{trans}$C=C—r) and 3.12 (t, CH₂—Ar).

For the mass spectrometric analysis, the product (6) had to be silylated. The mass of the silylated compound (6), actually compound (5) in the Scheme 1, was m/e$_{exp}$. 594.2002 and m/e$_{theor}$. 594.2003.

It was not possible to determine a clear melting point for the compound (6).

EXAMPLE 2

Preparation of functionalized styrene polymers

Three surface functionalized polymers were made by polymerizing styrene, a crosslinking monomer and the functional monomer according to the Example 1. In all the polymers, the concentration of crosslinking agent was 20 mole-%.

The polymer 1 was made using the solvent method with butanol as pore forming solvent. The crosslinking agent was bis(vinylphenyl)ethane. 2.5 g of a 20:80 bis(-vinylphenyl)ethane styrene mixture was dissolved in 2.5 g of butanol in a 10 ml test tube. 0.82 g of functional monomer and 0.033 g of AIBN was added. The test tube was sealed with a stopper penetrated by a capillary needle after which the sample was allowed polymerize at 60° C. for 12 h.

Polymer 2 was made from a water/sodium (ethylhexyl)sulfosuccinate/styrene microemulsion using divinylbenzene as the crosslinking agent. 0.375 g of AOT was dissolved in 2.5 g of a 20:80 divinylbenzene styrene mixture. 0.14 g of ion exchanged water was added under vigorous stirring. 0.55 g of functional monomer was added to the microemulsion in a 10 ml test tube and thermostated to 30° C. for 15 minutes or until the optically clear microemulsion showed no sign of unsolubilized monomer. 0.03 g of AIBN was added to the sample after which the test was sealed with a rubber stopper penetrated by a capillary needle. The microemulsion was allowed to polymerize at 60° C. for 12 h.

The polymer 3 was made in a manner similar to the polymer 2, but using bis(vinylphenyl)ethane as the crosslinking agent.

The polymer plugs were removed, ground in a laboratory mill fitted with a 1 mm filter, extracted with methanol and toluene and dried thoroughly under vacuum. The 0.125–0.5 mm fraction was separated for further use.

The phosphorus concentration in all the three polymers was determined with elementary analysis. Polymer 1 had a phosphorous content of 0.33 mmol/g, polymer 2 0.48 mmol/g and polymer 3 0.45 mmol/g.

EXAMPLE 3

Determination of the amount of functional groups available on the pore surfaces

The porous polymers made according to the Example 2 are packed into a column using a KOH-solution. The three columns are rinsed with water to a neutral pH.

The degree of phosphonic acid groups in the surface of the polymers is determined by measuring the capacity of the porous polymer of complexing to copper from an aqueous solution.

A CuCl$_2$-solution was fed for three hours during the columns. Thereafter they are rinsed for as long a time with ion-changed water. The copper is dissolved by eluting with 100 ml of 1M HCl. The copper concentration in the acid solution is determined with plasma emission spectrophotometry. A small amount of the copper functionalized polymers are dried under vacuum and analyzed with ESCA (Electron spectroscopy for chemical analysis) for its surface composition. The results are collected in the following table:

Results of the surface functionalization tests

| Polymer Nr | P mmole/g | Cu$^{++}$ disc. DCP ppm | with HCl Theor ppm | In the surface % |
|---|---|---|---|---|
| 1 | 0.33 | 119.9 | 184.9 | 65 |
| 2 | 0.48 | 166.1 | 223 | 75 |
| 3 | 0.45 | 144.7 | 194 | 75 |

A surprisingly high proportion of the functional groups are present at pore surfaces available to the water phase. ESCA analysis at a 60° angle show about 2 atom-% phosphorus and a Cu/P-ratio of 1 for all three polymers. It may be mentioned from the literature that only 0.6% of the functional groups in a 400 mesh ground polymer were available for an aqueous solution.

EXAMPLE 4

Preparation of a polymer bound palladium catalyst 1.2045 g of styrene, 1.0022 g of divinylbenzene, 0.3894 g of sodium (ethylhexyl)sulfosuccinate are dissolved in the polymerization vessel. To the monomer solution, 0.1103 g of water is added. The mixture is shaken until a completely clear solution is obtained. In the microemulsion 0.2078 of 1-(3-vinylphenyl)propane-2,2-bisphosphonic acid is dissolved. The microemulsion is polymerized at 60° C. using AIBN as initiator.

The polymer is extracted in methanol and dried in vacuum. In a glass column the polymer is rinsed with a KOH-solution and water to pH 7. Palladium is complexed to the polymer by feeding a PdCl$_2$-solution through the column. The excess of PdCl$_2$ is rinsed off with water during three hours. The colour of the polymer is now grey-black. The catalyst is examined with ESCA. The composition of the surface is: carbon 83.7%, oxygen 12.06%, phosphorus 2.2% and palladium 2.0%. The material is also examined with energy dispersive X-ray analysis (EDXA) before the hydrogenation tests and after two hydrogenations.

It can be determined that the ratio between phosphorus and palladium is constant, both before hydrogenation as well as after ten hydrogenations. With the cathode voltage used, EDXA analyses the composition of the polymer to a depth of appr. 1 μm. As the polymer is 20% crosslinked, and does not swell in the solvents used, the catalytically active groups are located at the pore surfaces.

EXAMPLE 5

Hydrogenation of 1-octene catalyzed by polymer bound palladium

Before use, the surface functionalized polymer bound palladium(II) catalyst, made according to the Example 4, and containing ca 0.4 mmoles of palladium per gram, was treated with hydrogen in order to reduce palladium(II) to palladium(O), by suspending it in methanol and passing hydrogen gas therethrough for two hours.

The hydrogenations of 1-octene were carried out in a 100 ml round-bottomed flask. The vessel was thermostated to 30° C., provided with a magnetic stirrer and connected to a gas burette that maintained the reaction at constant 1 atm hydrogen pressure. In the reaction vessel 0.2645 g of the dried palladium catalyst and 45.00 ml of methanol were placed. Stirring was started and the air in the system was displaced by repeating the process of evacuating and flushing with hydrogen three times. Finally, an adequate amount of hydrogen gas was stored in the gas burette, and the mixture was stirred 15-30 min to saturate the solution with hydrogen. The stirring was discontinued and 5.00 ml of a 0.995 M 1-octene solution in methanol was injected into the reaction vessel. The reaction was initiated by starting the stirrer. The stirring speed was 1000 rpm. The progress of the hydrogenation was followed by recording the hydrogen uptake vs. time. The initial rates of the hydrogenations as a measure of the catalytic activity were calculated from the slope of the amount of hydrogen absorbed versus the reaction time. The catalyst was easily recovered from the reagents by filtration and was reused after washing with methanol and drying in vacuum.

The reaction rates and the activity of the catalyst varied only by 5% over ten runs. The rate was 50 ml/min per gram of catalyst.

EXAMPLE 6

Preparation of a polymer bound ruthenium catalyst 1.22 g of divinylbenzene, 1.47 g of styrene, 0.506 g of AOT are dissolved in the polymerisation vessel. To the monomer solution, 0.168 g of water is added. The mixture is shaken until a completely clear solution is obtained. In the microemulsion, 0.2748 g of 1-(3-vinylphenyl)propane-2,2-bisphosphonic acid is dissolved. The microemulsion is polymerized at 60° C. using AIBN as initiator.

The polymer is extracted in methanol and dried in vacuum. In a glass coloumn the polymer is rinsed with a KOH-solution and water to pH 7. Ruthenium is complexed to the polymer by feeding a 50 ppm $RuCl_3$ solution through the coloumn. The excess of ruthenium is rinsed off with water. The polymer is examined with energy dispersive x-ray analysis to determine the ruthenium/phosphorous ratio. This ratio was found to be equal to 1 as also the ruthenium/phosphorous ratio on the surface of the polymer determined by ESCA. As the polymer is 20% crosslinked, and does not swell in the solvents used, the surface functionalization percentage should be 100 %.

EXAMPLE 7

Preparation of crosslinking agents

1. Preparation of 1,2-(vinylphenyl)ethane

In a flame dried 250 ml two-necked flask, provided with a magnetic stirrer, and fitted with a reflux condenser, a dropping funnel and calcium chloride protection tubes, was placed 2.43 g (0.10 moles) magnesium turnings and a few crystals of iodine. The flask was heated, using a Bunsen burner, until the iodine started to evaporate and a red colour appeared. The mixture was allowed to cool slightly and vigorous stirring was started. 15.3 g (0.10 moles) of vinylbenzyl chloride dissolved in 100 ml of tetrahydrofurane was dropped at such a rate that the solvent boiled continuously. Immediately when the most vigorous reaction stage had passed the hot solution was poured into slightly acidic (HCl) ice water. The white precipitate formed in the mixture was filtered, and the filtrate was extracted three times with chloroform. The organic phase was dried over sodium sulfate and concentrated on a rotary vacuum evaporator. The evaporation residue was washed with hot diisopropyl ether, and the oily yellow residue collected at the bottom was separated by decanting.

The residue was concentrated and 10.4 g (89 %) of >90% pure product was obtained. The raw product is easily purified by flash chromatography. Regarding the $^1H$ NMR spectrum it is to be noted that the vinylbenzyl chloride used as starting material was a mixture of the meta- and para-forms (7:3). Thus the product formed was a mixture of three isomers of 1,2-(vinylphenyl)ethane (about 5:4:1) which was also evident from the $^1H$ NMR spectrum and gas chromatogram of the product. $^1H$ NMR-spectrum of the main isomer (meta); ($CDCl_3$, 400 MHz) 7.32-6.99 (m, 8H, Ar), 6.65 (dd, 2H, $=CH-Ar$, $J_{trans}=17.4$, $J_{cis}=11.0$), 5.70 (d, 2H, $H_{cis}C=C-Ar$, $J_{trans}=17.4$), 5.19 (d, 2H, $H_{trans}C=C-Ar$, $J_{cis}=11.0$) and 2,84 (s, 4H, $CH_2-Ar$).

2. Preparation of bis(vinylbenzyloxy)alkanes

The following new bis(vinylbenzyloxy)alkanes were prepared (formula II, m=1): m'=2 (compound 1), m'=6 (compound 2) and m'=12 (compound 3).

For example compound (3) was prepared in the following manner. In a flame dried reaction flask, protected with nitrogen gas, was placed 10.0 g (0.049 moles) of 1,12-dodecanediol and 100 ml of tert.-butanol. The stirring was started, and the mixture warmed to 30° C. until the solution became clear. The temperature of the mixture was thereafter kept at 30° C. 12.8 g (0.114 moles) of potassium tert.-butylate was added, and the stirring was continued over night in order to ensure the formation of the dipotassium salt of the diol. Then 17.3 g (0.114 moles) of vinylbenzyl chloride was dropped into the mixture. When the addition was complete, stirring was continued for one day. The mixture was treated with a dilute phosphoric acid solution and extracted three times with chloroform. The organic phase was washed with water, dried over sodium sulfate and concentrated in vacuum.

The product was crystallized from diisopropyl ether and 8.12 g (38 %) of pure 1,12-di(vinylbenzyloxy)dodecane (3) was obtained; mp 17° C. (DSC); $^1H$ NMR ($CDCl_3$, 400 MHz) 7.41-7.19 (m, 8H, Ar), 6.70 (dd, 2H, $=CH-Ar$, $J_{trans}=17.3$, $J_{cis}=10.7$), 5.75 (d, 2H, $H_{cis}C=C-Ar$, $J_{trans}=17.3$), 5.23 (d, 2H, $H_{trans}C=C-Ar$, $J_{cis}=10.7$), 4.48 (s, 4H, $ArCH_2O$), 3.45 (t, 4H, $OCH_2CH_2$, J=6.8), 1.65 (distorted quintet, 4H, $OCH_2CH_2$, J=6.9) and 1.39-1.22 (m, 16H, $(CH_2)_8$); $m/e_{theor}$.434.3185 and $m/e_{exp}$. 434.3172.

The compounds (1) and (2) were synthesized in a similar way. The compound (1) was not crystallized. The pure compound (2) was obtained in 29 % yield; $^1H$ NMR ($CDCl_3$) 7.40-7.19 (m, 8H, Ar), 6.69 (dd, 2H, $=CHAr$, $J_{trans}=17.6$, $J_{cis}=10.9$), 5.73 (dd, 2H, $H_{cis}C=C-Ar$, $J_{trans}=17.6$, $J_{gem}=0.8$), 5.21 (dd, 2H, $H_{trans}C=C-Ar$, $J_{cis}=10.9$, $J_{gem}=0.8$), 4.45 (s, 4H, $ArCH_2O$), 3.43 (t, 4H, $OCH_2CH_2$, J=6.6), 1.65- 1.55 (m, 4H, $OCH_2CH_2$) and 1.45-1.30 (m, 4H, $OCH_2CH_2CH_2$); $m/e_{theor}$. 350.2246 and $m/e_{exp}$. 350.2238

EXAMPLE 7

Comparison of the mechanical strength of crosslinked styrene polymers

Monomer mixtures of styrene and 1, 2, 5, 10, 20 and 30 mole-% of the crosslinking divinyl monomers were made. Three different divinyl monomers were used 1,2-bis(vinylphenyl)ethane and 1,6-di(vinylbenzyloxy)-hexane according to example 7 and divinylbenzene. The initiator AIBN, 0.5 wt-% based on monomers, was added after which the solutions were bubbled with nitrogen for 15 min. The monomer mixtures were allowed to polymerize at 70° C. for 10 h in a glass sealed teflon mould. The mould was dimensioned for a 25 mm * 2 mm * 2 mm polymer rod.

The brittle nature of many styrene polymers makes a three point bending test particularly useful for evaluation of differences in the mechanical behaviour between differently crosslinked polymers. The polymer rod was deformed by a triangular steel blade to an increasing compression, and the respective force was determined until the rod failed. Stress at break was calculated and compared for polymers crosslinked on an equal molar basis, but with different divinyl monomer.

The divinylbenzene crosslinked polymer had such a low bending strength (<<20 MPa), at crosslinking degrees commonly used for the manufacture of macroporous polymers (over 15 mole-%), that it was not possible to remove the test body from the mould. The polymers with 1,2-bis(vinylphenyl)ethane and 1,6-di(-vinylbenzyloxy)hexane, on the other hand, had bending strengths between 65 and 95 MPa at crosslinking degrees of 2,5 to 30%.

EXAMPLE 8

Synthesis of a styrene 1-(3-vinylphenyl)propane-2,2-bisphosphonic acid copolymer 0.6943 g of styrene, 1.3211 g of 1-(3-vinylphenyl)-propane2,2-bisphosphonic acid and 0.01 g of AIBN was dissolved in hexanol. Through the solution nitrogen was bubbled for fifteen minutes, whereafter it was allowed to polymerize for 12 h at 60° C. The solid polymer was separated from the hexanol phase, washed with pure hexanol and dried thoroughly for 24 h in vacuum. The polymer was characterized with FTIR.

We claim:

1. In a process for making a surface functionalized macroporous styrene polymer wherein styrene monomer units are polymerized in the presence of a divinyl cross linking agent and a surfactant in a water in-monomer microemulsion, the improvement comprising admixing with the microemulsion as a functionalizing agent a bisphosphonic acid derivative having the formula:

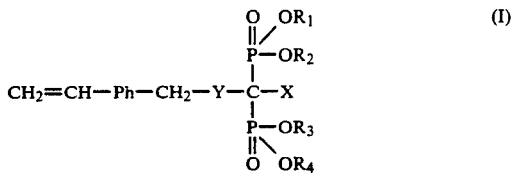

wherein each one of the groups $R_1$, $R_2$, $R_3$ and $R_4$ is independently selected from the group consisting of hydrogen, lower alkyl, $-CH_2CH_2OH$ or $R_1$ and $R_2$ are together $-CH_2CH_2-$, or $R_3$ and $R_4$ are together $-CH_2CH_2-$;

X is selected from the group consisting of hydrogen, methyl, ethyl and COOH;

Y is selected from the group consisting of an optionally unsaturated alkylene group $(CH_2)_n-$ where n has the value 0 to 12, $-OCH_2CH_2O$, $-OCH_2C^*-H(OH)CH_2-$, wherein the carbon atom marked with * is chiral and is in a form selected from the group consisting of the R-form, S form, and a racemate; and Ph is a phenyl group which carries the vinyl group in meta or para position to the methylene group; and, reacting the mixture to form a macroporous styrene polymer functionally modified with the bisphosphonic acid derivative.

2. The process of claim 1 further comprising, in a subsequent step, forming the functionally modified macroporous polymer into a metal salt or a metal complex.

3. The process of claim 2 wherein the metal salt or metal complex is formed by an ion-exchange reaction.

4. The process of claim 1 wherein the bisphosphonic acid derivative is first formed into a metal salt or a metal complex form and then admixed with the microemulsion.

5. The process of claim 1 wherein each one of the groups $R_1$, $R_2$, $R_3$ and $R_4$ of the bisphosphonic acid derivative admixed with the microemulsion is selected from the group consisting of lower alkyl, $-CH_2CH_2OH$, or $R_1$ and $R_2$ are together $-CH_2CH_2-$ and $R_3$ and $R_4$ are together $-CH_2CH_2-$ and wherein the functionally modified macroporous styrene polymer formed from the reaction is subjected to a hydrolysis reaction to convert at least one of the groups $R_1$-$R_4$ to hydrogen.

6. The process of claim 5 further comprising, in a subsequent step, forming the hydrolyzed and functionally modified polymer into a metal salt or a metal complex.

7. The process of claim 6 wherein the metal salt or metal complex is formed by an ion-exchange reaction.

8. The process of claim 2 wherein the metal is a transition metal.

9. The process of claim 4 wherein the metal is a transition metal.

10. The process of claim 1 wherein the bisphosphonic acid derivative is 1-(3-vinylphenylpropane) 2,2-bisphosphonic acid.

11. The process of claim 1 wherein the bisphosphonic acid derivative is admixed in amount of up to 20 percent by weight of the total amount of monomer in the mixture.

12. The process of claim 1 wherein the surfactant is sodium bis(2-ethylhexyl) sulfosuccinate.

13. The process of claim 1 wherein the cross-linking agent is a compound having the formula:

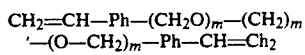

wherein m is 0 or 1, and when m is 0, m' is 1-12, and when m is 1, m' is 2-12, the vinyl groups on the phenyl groups of the compound being in a meta or a para position on the phenyl groups with respect to the methylene groups bonded to the phenyl groups.

14. The process of claim 1 wherein the cross-linking agent is a compound having the formula:

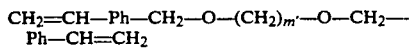

wherein m' is 2-12 and the vinyl groups on the phenyl groups of the compound are in a meta or a para position on the phenyl groups with respect to the methylene groups bonded to the phenyl groups.

15. The process of claim 1 wherein the cross-linking agent is divinyl benzene.

16. The process of claim 13 wherein the cross linking agent is 1,2 bis(vinyl phenyl) ethane.

* * * * *